US006423852B1

(12) United States Patent
Umetani et al.

(10) Patent No.: US 6,423,852 B1
(45) Date of Patent: Jul. 23, 2002

(54) PROCESS FOR THE PREPARATION OF TRIFLUOROTHYMIDINE DERIVATIVES

(75) Inventors: Hideki Umetani; Nobuyuki Fukazawa; Hironori Komatsu, all of Chiba (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/958,298

(22) PCT Filed: Feb. 9, 2001

(86) PCT No.: PCT/JP01/00945

§ 371 (c)(1),
(2), (4) Date: Oct. 9, 2001

(87) PCT Pub. No.: WO01/58917

PCT Pub. Date: Aug. 16, 2001

(30) Foreign Application Priority Data

Feb. 10, 2000 (JP) .......................................... 2000-33202

(51) Int. Cl.$^7$ .............................................. C07D 239/02
(52) U.S. Cl. ....................................................... 549/429
(58) Field of Search ......................................... 544/309

(56) References Cited

FOREIGN PATENT DOCUMENTS

| EP | 0389110 A2 | 9/1990 |
| JP | 0635417 A1 | 1/1995 |

*Primary Examiner*—Amelia Owens
(74) *Attorney, Agent, or Firm*—Burns, Doane, Swecker & Mathis, L.L.P.

(57) ABSTRACT

5-trifluoromethyl-2,4-bis(trimethylsilyloxy)pyrimidine is reacted with a 2-deoxy-α-D-erythro-pentofuranosyl chloride derivative reacted in the absence or presence of a small amount of solvent to give a β-form of 1-(2'-deoxy-β-D-erythro-pentofuranosyl)-5-trifluoromethyl uracil derivative with a high selectivity.

30 Claims, No Drawings

PROCESS FOR THE PREPARATION OF TRIFLUOROTHYMIDINE DERIVATIVES

TECHNICAL FIELD

This invention relates to a process for preparing a 1-(2'-deoxy-β-D-erythro-pentofuranosyl)-5-trifluoromethyl uracil derivative exhibiting antitumor and antiviral activities.

BACKGROUND ART 1-(2'-deoxy-β-D-erythro-pentofuranosyl)-5-trifluorom ethyluracil derivatives (trifluorothymidine derivatives) have attracted attention for many years in terms of their association with nucleic acid bases, uridine and thymidine. In particular, since they exhibit antitumor and antiviral activities, they have been intensely investigated for production as a medical drug or an important intermediate therefor. It is well known in this art that a preparation process considerably depends on the type of a nucleic acid base and that a superior preparation process must be studied for each base.

For example, as described in Nucleic Acid Research 12 6827 (1984) and Nucleosides & Nucleotides 8 549 (1989), a nucleic acid base such as uracil, fluorouracil, thymine and trifluorothymine drastically changes its properties, depending on a substituent on the 5-position. Thus, in its preparation by glycosylation, a process suitable to each reaction must be investigated. In particular, in 5-trifluorouridine, to which this invention is directed, the trifluoromethyl group significantly influences to give the chemical properties of the compound greatly different from unsubstituted uridine or thymidine and reduces a selectivity between α- and β-forms in glycosylation. It has been, therefore, difficult to establish an industrial process for preparing the β-form which is practically needed.

Conventional processes for preparing a 1-(2'-deoxy-β-D-erythro-pentofuranosyl)-5-trifluoromethyl uracil derivative are;

(1) exchanging a nucleic acid base from thymidine and 5-trifluoromethyluracil by, for example, nucleoside-2'-deoxyribose transferase [M. G. Stout, et al., Methods Carbohydr. Res., 7, 19 (1976)];

(2) reacting a halogen atom on the 5-position in a 1-(2'-deoxy-β-D-erythro-pentofuranosyl)-5-halouracyl derivative with trifluoromethyl copper [Y. Kobayashi, et al., J. C. S. Perkin TransI, 2755 (1980)];

(3) electrolysis of an uridine derivative and trifluoroacetic acid [L. Hein, et al., DE 119423 (1976)];

(4) reacting 5-trifluoromethyl-2,4-bis(trimethylsilyloxy) pyrimidine with a methyl 2-deoxy-D-erythro-pentofuranoside derivative in the presence of an acid catalyst [National Publication of the International Patent Application No. 500239-1987];

(5) increasing a molar ratio of 5-trifluoromethyl-2,4-bis (trimethylsilyloxy)pyrimidine in its reaction with 3,5-di-O-(p-chlorobenzoyl)-2-deoxy-α-D-erythro-pentofuran osyl chloride or conducting the reaction in the presence of a zinc chloride catalyst [Japanese Patent Laid-Open No. 2-289595; Heterocycles, 31, 569 (1990)].

However, the process described in (1) has a drawback that it is difficult to isolate and purify the desired product from a reaction system. The process, therefore, cannot be suitably applied to large scale synthesis. The process described in (2) has a drawback that a reaction intermediate is quite sensitive to, for example, air. The process described in (3) has a drawback that both yield and current efficiency are low and electric facilities resistant to trifluoroacetic acid are required.

The process described in (4) has a drawback that a product is obtained as a mixture of α- and β-forms which cannot be readily separated so that an isolation yield for the desired β-form is extremely low.

For the process described in (5), referring to the reaction analysis values described in the literature, one mole of 3,5-di-O-(p-chlorobenzoyl)-2-deoxy-α-D-erythro-pentofuran osyl chloride is treated dropwise with a solution of two moles of 5-trifluoromethyl-2,4-bis(trimethylsilyloxy) pyrimidine in chloroform (on the basis of calculation from the values in the literature, an 11.1-fold amount of chloroform to the total amount of 3,5-di-O-(p-chlorobenzoyl)-2-deoxy-α-D-erythro-pentofuran osyl chloride and 5-trifluoromethyl-2,4-bis(trimethylsilyloxy)pyrimidine) to give a selectivity of β/α form=56/44 while being treated with 8 moles to give a selectivity of β/α form=74/26.

Zinc chloride may be added instead of increasing a molar ratio of 5-trifluoromethyl-2,4-bis(trimethylsilyloxy) pyrimidine to 3,5-di-O-(p-chlorobenzoyl)-2-deoxy-α-D-erythro-pentofuran osyl chloride to improve a selectivity of β/α form=about 75/25. The process has an economically and industrially significant drawback that it uses a largely excessive amount of quite expensive 5-trifluoromethyl-2,4-bis (trimethylsilyloxy)pyrimidine and either procedure cannot give a practical β-selectivity.

Thus, no conventional preparation processes can be suitably applied to stable and low-cost large scale production of a 1-(2'-deoxy-β-D-erythro-pentofuranosyl)-5-trifluoromethyl uracil derivative important as a medical drug or an intermediate therefor and an improved and useful process has been needed.

DISCLOSURE OF THE INVENTION

An objective of this invention is to solve the above problems in conventional preparation processes and provide a process for preparing a 1-(2'-deoxy-β-D-erythro-pentofuranosyl)-5-trifluoromethyl uracil derivative with an improved-selectivity by lower-cost and convenient steps.

We have investigated preparation of a 1-(2'-deoxy-β-D-erythro-pentofuranosyl)-5-trifluoromethyl uracil derivative by reacting 5-trifluoromethyl-2,4-bis(trimethylsilyloxy) pyrimidine with a 2-deoxy-α-D-erythro-pentofuranosyl chloride derivative and have found that in a solvent free system the reaction may proceed with a very high selectivity of β/α form=96/4. We have also found that a solvent may be added up to a 4-fold mass to the total mass of the reactants for avoiding a tendency to difficulty in stirring due to increased viscosity of the reactants as the reaction proceeds in the solvent free reaction to ensure smooth stirring and good operability and to provide the β-form of the desired product, the 1-(2'-deoxy-β-D-erythro-pentofuranosyl)-5-trifluoromethyl uracil derivative, with an improved selectivity. This invention has been achieved on the basis of these findings.

One aspect of a process for preparing a trifluorothymidine derivative according to this invention comprises the step of reacting 5-trifluoromethyl-2,4-bis(trimethylsilyloxy) pyrimidine represented by formula (1):

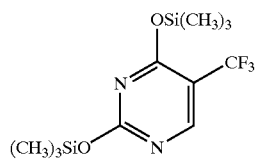
(1)

as a first material, with a 2-deoxy-α-D-erythro-pentofuranosyl chloride derivative represented by formula (2):

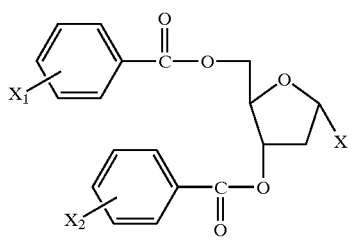
(2)

wherein X represents a halogen atom; $X_1$ and $X_2$ independently represent a hydrogen atom, methyl group or halogen atom, as a second material in a solvent free system to give a 1-(2'-deoxy-β-D-erythro-pentofuranosyl)-5-trifluoromethyl uracil derivative represented by formula (3):

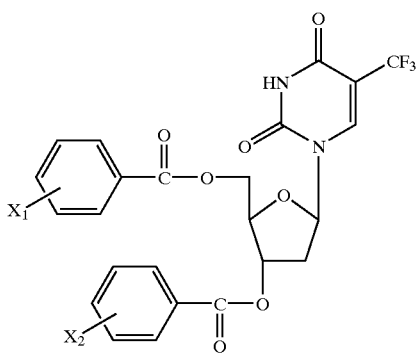
(3)

Another aspect of a process for preparing a trifluorothymidine derivative according to this invention comprises the step of reacting 5-trifluoromethyl-2,4-bis(trimethylsilyloxy)pyrimidine represented by formula (1):

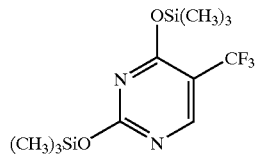
(1)

as a first material, with a 2-deoxy-α-D-erythro-pentofuranosyl chloride derivative represented by formula (2):

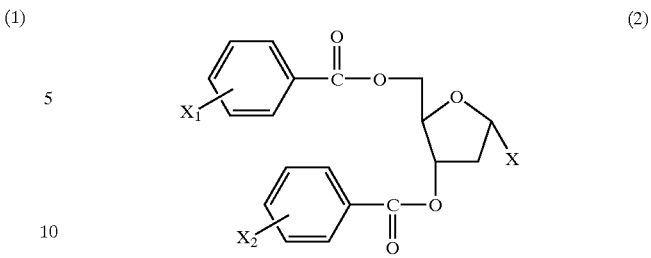
(2)

wherein X represents a halogen atom; $X_1$ and $X_2$ independently represent a hydrogen atom, methyl group or halogen atom, as a second material in the presence of a solvent to give a 1-(2'-deoxy-β-D-erythro-pentofuranosyl)-5-trifluoromethyl uracil derivative represented by formula (3):

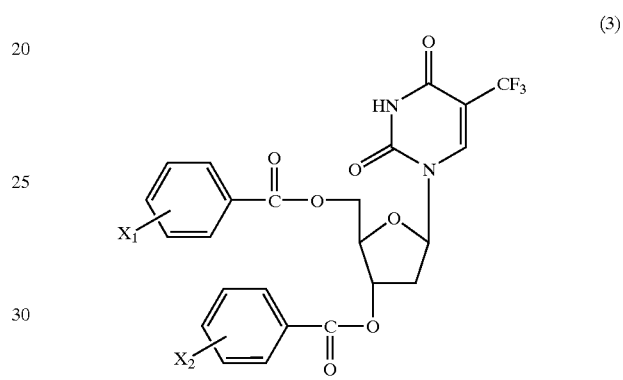
(3)

in which the solvent is used in an amount not exceeding a 4-fold mass to the total mass of the first and the second materials.

In the process of the first aspect of this invention, the reaction may be initiated in a solvent free system and then a solvent may be added to the reaction system to conduct the reaction in the presence of the solvent.

According to this invention, since the reaction stoichiometrically proceeds, materials unstable in the air may be used in a needed amount, resulting in effective use of the materials and elimination of a step for recovering remaining materials.

BEST MODE FOR CARRYING OUT THE INVENTION

This invention will be described in detail.

Two starting materials are used in a preparation process according to this invention. First, 5-trifluoromethyl-2,4-bis(trimethylsilyloxy)pyrimidine as a first material may be readily prepared by a known procedure from a known compound, 5-trifluoromethyluracil (See, for example, T. A. Khawaja, et al., J. Med. Chem., 12, 543 (1969)).

A 2-deoxy-α-D-erythro-pentofuranosyl chloride derivative as a second material may be also prepared in several steps by a known process from a readily available starting material, 2-deoxyribose. For example, as a representative example, 3,5-di-O-(p-chlorobenzoyl)-2-deoxy-α-D-erythro-pentofuran osyl chloride may be prepared using 2-deoxyribose as a starting material according to J. J. Fox, et al., J. Am. Chem. Soc., 83, 4066 (1961).

A molar ratio of the first/the second materials used in this invention is preferably 0.5 to 2 both inclusive, and economically the upper limit of the range is more preferably 1.

The reaction between the first and the second materials in this invention is conducted in the absence or presence of a solvent in a given amount or less. There are no restrictions to a solvent used in this invention as long as it is aprotic. Preferable examples of such an aprotic solvent include aromatic solvents such as 1,2,4-trichlorobenzene, o-dichlorobenzene, chlorobenzene, anisole, toluene and nitrobenzene; ethers such as diisopropyl ether, diethyl ether, tetrahydrofuran and dioxane; esters such as ethyl acetate; ketones such as acetone, methyl ethyl ketone and methyl isobutyl ketone; halogenated aliphatic solvents such as chloroform and methylene chloride. A solvent may be constituted by at least one of these. Halogenated aromatic solvents such as 1,2,4-trichlorobenzene, o-dichlorobenzene and chlorobenzene are herein categorized in aromatic solvents. More preferable solvents include 1,2,4-trichlorobenzene, o-dichlorobenzene, chlorobenzene, anisole, toluene and methyl isobutyl ketone.

The amount of a solvent used is up to 4-fold to the total mass of the first and the second materials, more preferably up to the total mass of the first and the second materials. If the amount is more than 4-fold, a β-selectivity may be reduced so that the objective of this invention cannot be achieved.

A solvent may be added to the reaction system after premixing it with at least one of the first and the second materials. A solvent may be added immediately after blending the first and the second materials or while the reaction proceeds after blending the first and the second materials.

An additive such as metal salts, ammonium salts and acids may be added to the reaction system. A metal salt maybe copper fluoride, zinc chloride or tin chloride. An ammonium salt may be tetrabutylammonium fluoride. An acid may be nitrophenol or trifluoromethylsilyl trifluoromethanesulfonate.

A reaction temperature may be −10° C. to a boiling point of a solvent used, preferably an ambient temperature to 70° C. both inclusive. At a temperature lower than an ambient temperature, the reaction may be slow, while at a temperature higher than 70° C. starting materials and/or a product may be decomposed a side reaction may occur. The reaction is generally completed in 0.5 to 48 hours.

It is surprising that a β selectivity and a yield can be improved in the absence or presence of a small amount of solvent in spite of an equimolar reaction, as apparent from Example 2 described later. The process according to this invention is very advantageous as an industrial preparation process for 1-(2'-deoxy-β-D-erythro-pentofuranosyl)-5-trifluoromethyl uracil derivatives in the light of improvement not only in effective material utilization but also in a reaction volume ratio. Furthermore, this is the first case where the derivative is prepared in the solvent free system. In addition, this is an extremely rare case where there are substantially no restrictions to the type of a solvent as long as its amount is small. These constitute characteristics of this invention.

A 1-(2'-deoxy-β-D-erythro-pentofuranosyl)-5-trifluoromethyl uracil derivative may be readily converted into 1-(2'-deoxy-β-D-erythro-pentofuranosyl)-5-trifluoromethyl uracil (trifluorothymidine) important as a medical drug or an intermediate therefor by a known method in a literature such as alkaline hydrolysis.

EXAMPLE

This invention will be more specifically described with reference to, but not limited to, Examples.

Hereinafter, 5-trifluoromethyl-2,4-bis(trimethylsilyloxy) pyrimidine, 3,5-di-O-(p-chlorobenzoyl)-2-deoxy-α-D-erythro-pentofuran osyl chloride, and 1-[3',5'-di-O-(p-chlorobenzoyl)-2'-deoxy-D-erythro-pentof uranosyl]-5-trifluorouracil are designated as Compounds I, II, and III, respectively. The reaction product, 1-[3',5'-di-O-(p-chlorobenzoyl)-2'-deoxy-β-D-erythro-pent ofuranosyl]-5-trifluoromethyluracil was identified by appropriate methods such as NMR analysis, melting point determination and HPLC analysis. A ratio of β/α form is a molar ratio.

Example 1

Glycosylation in a solvent free system

To 1.05 g of Compound I (3.24 mmol) was added 1.39 g of Compound II (3.24 mmol) and the mixture was reacted at 50° C. for 4 hours to give Compound III in an yield of 83% with a ratio of β/α form=95/5. Then, to the reaction product was added 5 ml of ethanol. The mixture was refluxed and cooled to room temperature, and the precipitate was collected by filtration to isolate Compound III with a ratio of β/α form=96/4. A yield of Compound III was 1.44 g.

Example 2 and

Comparative Example 1

Influence of material concentrations in glycosylation reaction

In the process described in Example 1, O-dichlorobenzene was added to make a mass ratio of O-dichlrobenzene to a total of (Compound I+Compound II) 0.54, 1.50, 3.72 or 11.32, and the mixture was reacted at 50° C. for 4 hours. After completion of the reaction, the reaction mixture was analyzed by HPLC to determine the effect of an initial material concentration in a reaction system containing a solvent on the glycosylation reaction. The results are shown in Table 1 together with those for Example 1.

TABLE 1

|  | Amount of a solvent (Solvent/Materials by weight) | β-Selectivity (%) | α-Selectivity (%) | (α + β) Yield (%) |
| --- | --- | --- | --- | --- |
| Example 1 | Neat | 95 | 5 | 83 |
| Example 2-1 | 0.54 | 90 | 10 | 83 |
| Example 2-2 | 1.50 | 86 | 14 | 82 |
| Example 2-3 | 3.72 | 83 | 17 | 81 |
| Comparative Example 1 | 11.32 | 79 | 21 |  |

Example 3

Glycosylation at a high material concentration

To a mixture of 1.07 g of Compound I (3.29 mml) and 1.41 g of Compound II (3.29 mmol) was added 0.87 g of toluene (toluene/[(Compound I)+(Compound II)] by mass= 0.35). The mixture was stirred at 50° C. for 4 hours and analyzed by HPLC to show that Compound III was produced in a reaction yield of 87% with a ratio of β/α form=91/9. Then, to the reaction product was added 4 ml of ethanol. The solid was collected by filtration to isolate Compound III in an isolation yield of 66% (1.25 g) with a ratio of β/α form=99/1.

Example 4

A reaction was conducted as described in Example 3, substituting 1.11 g of chlorobenzene for 0.87 g of toluene (chlorobenzene/[(CompoundI)+(Compound II)]by mass= 0.45). Compound III was produced in a reaction yield of 85% by HPLC with a ratio of β/α form=91/9 and isolated in a yield of 74% (1.39 g) with a ratio of β/α form=91/9.

Example 5

To a mixture of 10.38 g of Compound I (33.35 mmol) and 13.75 g of Compound II (33.35 mmol) was added 13.06 g of o-dichlorobenzene (o-dichlorobenzene/[(Compound I)+ (Compound II)]by mass=0.54). The mixture was stirred at 50° C. for 4 hours and analyzed by HPLC to show that Compound III was produced in a reaction yield of 83% with a ratio of β/α form=90/10. Then, to the reaction product was added 30 ml of methanol. The mixture was refluxed and then cooled to room temperature. The precipitate was collected by filtration to isolate Compound III in an isolation yield of 53% (9.71 g) with a ratio of β/α form=>99/<1.

Example 6

A reaction was conducted as described in Example 3, substituting 1.45 g of 1,2,4-trichlorobenzene for 0.87 g of toluene (1,2,4-trichlorobenzene/[(Compound I)+ (Compound II)]by mass=0.59). Compound III was produced in a reaction yield of 83% by HPLC with a ratio of β/α form=93/7 and isolated in a yield of 70% (1.36 g) with a ratio of β/α form=93/7.

Example 7

To a mixture of 1.06 g of Compound I (3.25 mmol) and 1.40 g of Compound II (3.25 mmol) was added 0.73 g of diisopropyl ether (diisopropyl ether/[(Compound I)+ (Compound II)]by mass=0.30). The mixture was stirred at 50° C. for 4 hours and analyzed by HPLC to show that Compound III was produced in a reaction yield of 78% with a ratio of β/α form=83/17. Then, to the reaction product was added 7 ml of ethanol. The solid was collected by filtration to isolate Compound III in an isolation yield of 60% (1.12 g) with a ratio of β/α form=81/19.

Example 8

To a mixture of 10.82 g of Compound I (33.35 mmol) and 14.33 g of Compound II (33.35 mmol) was added 9.95 g of anisole (33.35 mmol) (anisole/[(Compound I)+(Compound II)]by mass=0.40). The mixture was stirred at 50° C. for 3hours and analyzed by HPLC to show that Compound III was produced in a reaction yield of 85% with a ratio of β/α form=92/8. Then, to the reaction product was added 40 ml of ethanol. After ice-cooling, the solid was collected by filtration to isolate Compound III in an isolation yield of 70% (13.37 g) with a ratio of β/α form=>99/<1.

Example 9

To a mixture of 1.09 g of Compound I (3.37 mol) and 1.45 g of Compound II (3.37 mmol) was added 0.90 g of ethyl acetate (ethyl acetate/[(Compound I)+(Compound II)]by mass=0.36). The mixture was stirred at 50° C. for 4 hours and analyzed by HPLC to show that Compound III was produced in a reaction yield of 82% with a ratio of β/α form=81/19. Then, to the reaction product was added 4 ml of ethanol. The solid was collected by filtration to isolate Compound III in an isolation yield of 66% (1.32 g) with a ratio of β/α form=80/20.

Example 10

To a mixture of 1.07 g of Compound I (3.29 mol) and 1.41 g of Compound II (3.29 mmol) was added 0.90 g of ethyl acetate (ethylacetate/[(CompoundI)+(CompoundII)] bymass=0.36). The mixture was stirred at room temperature for 44 hours and analyzed by HPLC to show that Compound III was produced in a reaction yield of 66% with a ratio of β/α form=88/12. Then, to the reaction product was added 4 ml of ethanol. The mixture was refluxed and cooled to room temperature. The solid was collected by filtration to isolate Compound III in an isolation yield of 52% (0.98 g) with a ratio of β/α form=>99/<1.

Example 11

A reaction was conducted as described in Example 9, substituting 1.20 g of nitrobenzene for 0.90 g of ethyl acetate (nitrobenzene/[(compound I)+(Compound II)]by mass= 0.47). Compound III was produced in a reaction yield of 82% by HPLC with a ratio of β/α form=81/19 and isolated in a yield of 62% (1.20 g) with a ratio of β/α form=79/21.

Example 12

To a mixture of 1.09 g of Compound I (3.37 mol) and 1.45 g of Compound II (3.37 mmol) was added 1.20 g of nitrobenzene (nitrobenzene/[(CompoundI)+(Compound II)] by mass=0.47). The mixture was stirred at room temperature for 24 hours and analyzed by HPLC to show that Compound III was produced in a reaction yield of 85% with a ratio of β/α form=86/14. Then, to the reaction product was added 4 ml of ethanol. The solid was collected by filtration to isolate Compound III in an isolation yield of 62% (1.20 g) with a ratio of β/α form=80/20.

Example 13

A reaction was conducted as described in Example 9, substituting 0.81 g of methyl ethyl ketone for 0.90 g of ethyl acetate (methyl ethyl ketone/[(Compound I)+(Compound II)]by mass=0.32). Compound III was produced in a reaction yield of 77% by HPLC with a ratio of β/α form=72/28 and isolated in a yield of 66% (1.27 g) with a ratio of β/α form=69/31.

Example 14

A reaction was conducted as described in Example 3, substituting 1.49 g of chloroform for 0.87 g of toluene (chloroform/[(Compound I)+(Compound II)]by mass= 0.60). Compound III was produced in a reaction yield of 86% by HPLC with a ratio of β/α form=88/12 and isolated in a yield of 79% (1.48 g) with a ratio of β/α form=88/12.

Example 15

To a mixture of 1.05 g of Compound I (3.24 mol) and 1.39 g of Compound II (3.24 mmol) was added 1.49 g of chloroform (chloroform/[(Compound I)+(Compound II)]by mass=0.61). The mixture was stirred at room temperature for 24 hours and analyzed by HPLC to show that Compound III was produced in a reaction yield of 86% with a ratio of β/α form=90/10. Then, to the reaction product was added 4 ml of ethanol. The solid was collected by filtration to isolate Compound III in an isolation yield of 82% (1.53 g) with a ratio of β/α form=91/9.

Example 16

Addition of a solvent in the course of a reaction

A mixture of 1.06 g of Compound I (3.27 mol) and 1.40 g of Compound II (3.27 mmol) was reacted at 50° C. for 1 hour. Then, to the slurry reaction mixture was added dropwise 1.00 g of anisole. The mixture was reacted at 50° C. for additional 3 hours. HPLC analysis showed that Compound III was produced in a reaction yield of 88% with a ratio of β/α form=94/6. Then, to the reaction product was added 4 ml of ethanol. The solid was collected by filtration to isolate 1.28 g of Compound III with a ratio of β/α form=99/1.

Industrial Applicability

According to this invention, a solvent free reaction can provide a very high selectivity of β/α form=96/4, which is significantly higher than that obtained by the prior art. Furthermore, a wide variety of solvents may be used as long as its amount is small and a practical β-selectivity can be achieved so that a highly universal preparation process can be provided.

Using the process according to this invention, expensive 5-trifluoromethyl-2,4-bis(trimethylsilyloxy)pyrimidine can be prepared by an equimolar reaction, which is an easy synthetic process with a good volume efficiency and is an industrial process with an improved economic efficiency.

What is claimed is:

1. A process for preparing a 1-(2'-deoxy-β-D-erythro-pentofuranosyl)-5-trifluoromethyl uracil derivative characterized by comprising the step of reacting 5-trifluoromethyl-2,4-bis(trimethylsilyloxy)pyrimidine represented by the following formula (1):

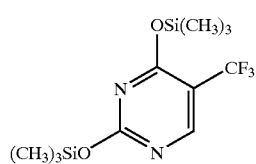
(1)

as a first material, with a 2-deoxy-α-D-erythro-pentofuranosyl chloride derivative represented by the following formula (2):

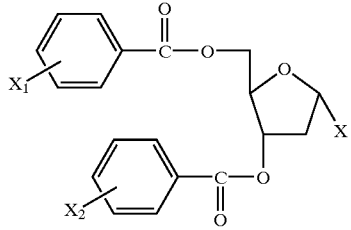
(2)

wherein X represents a halogen atom; $X_1$ and $X_2$ independently represent a hydrogen atom, methyl group or halogen atom, as a second material in a solvent free system to give a 1-(2'-deoxy-β-D-erythro-pentofuranosyl)-5-trifluoromethyl uracil derivative represented by the following formula (3)

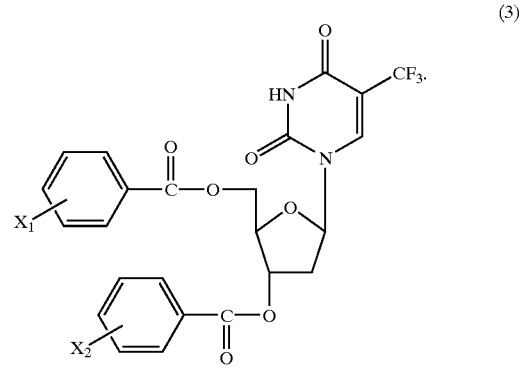
(3)

2. The process according to claim 1 characterized in that the reaction of said first material with said second material is conducted in the presence of a solvent in an amount of up to a 4-fold mass to the total mass of the first and the second materials.

3. A process for preparing a 1-(2'-deoxy-β-D-erythro-pentofuranosyl)-5-trifluoromethyl uracil derivative characterized by comprising the step of reacting 5-trifluoromethyl-2,4-bis(trimethylsilyloxy)pyrimidine represented by the following formula (1):

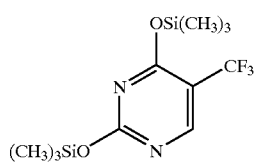
(1)

as a first material, with a 2-deoxy-α-D-erythro-pentofuranosyl chloride derivative represented by the following formula (2):

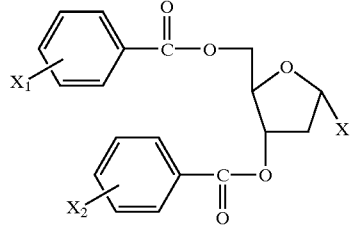
(2)

wherein X represents a halogen atom; $X_1$ and $X_2$ independently represent a hydrogen atom, methyl group or halogen atom, as a second material in the presence of a solvent to give a 1-(2'-deoxy-β-D-erythro-pentofuranosyl)-5-trifluoromethyl uracil derivative represented by the following formula (3):

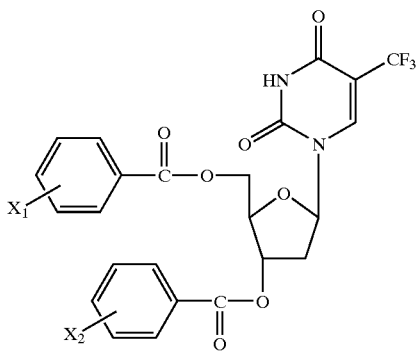

(3)

and characterized in that the solvent is used up to a 4-fold mass to the total mass of the first and the second materials.

4. The process according to claim 3, characterized in that said solvent is one or a combination of two or more selected from the group consisting of aromatic, ether, ester, ketone and halogenated solvents.

5. The process according to claim 4, characterized in that the aromatic solvent is one or two or more selected from the group consisting of 1,2,4-trichlorobenzene, o-dichlorobenzene, chlorobenzene, anisole, toluene and nitrobenzene.

6. The process according to claim 4, characterized in that the ether solvent is one or two or more selected from the group consisting of isopropyl alcohol, diethyl ether, tetrahydrofuran and dioxane.

7. The process according to claim 4, characterized in that the ester solvent is ethyl acetate.

8. The process according to claim 4, characterized in that the ketone solvent is one or two or more selected from the group consisting of acetone, methyl ethyl ketone and methyl isobutyl ketone.

9. The process according to claim 4, characterized in that the halogenated solvent is at least one of chloroform and methylene chloride.

10. The process according to claim 9, characterized in that the reaction of the first material with the second material is conducted in the presence of a metal salt, an ammonium salt or an acid.

11. The process according to claim 2, characterized in that said solvent is one or a combination of two or more selected from the group consisting of aromatic, ether, ester, ketone and halogenated solvents.

12. The process according to claim 11, characterized in that the aromatic solvent is one or two or more selected from the group consisting of 1,2,4-trichlorobenzene, o-dichlorobenzene, chlorobenzene, anisole, toluene and nitrobenzene.

13. The process according to claim 11, characterized in that the ether solvent is one or two or more selected from the group consisting of isopropyl alcohol, diethyl ether, tetrahydrofuran and dioxane.

14. The process according to claim 11, characterized in that the ester solvent is ethyl acetate.

15. The process according to claim 11, characterized in that the ketone solvent is one or two or more selected from the group consisting of acetone, methyl ethyl ketone and methyl isobutyl ketone.

16. The process according to claim 11, characterized in that the halogenated solvent is at least one of chloroform and methylene chloride.

17. The process according to claim 11, characterized in that the reaction of the first material with the second material is conducted in the presence of a metal salt, an ammonium salt or an acid.

18. The process according to claim 12, characterized in that the reaction of the first material with the second material is conducted in the presence of a metal salt, an ammonium salt or an acid.

19. The process according to claim 13, characterized in that the reaction of the first material with the second material is conducted in the presence of a metal salt, an ammonium salt or an acid.

20. The process according to claim 14, characterized in that the reaction of the first material with the second material is conducted in the presence of a metal salt, an ammonium salt or an acid.

21. The process according to claim 15, characterized in that the reaction of the first material with the second material is conducted in the presence of a metal salt, an ammonium salt or an acid.

22. The process according to claim 16, characterized in that the reaction of the first material with the second material is conducted in the presence of a metal salt, an ammonium salt or an acid.

23. The process according to claim 1, characterized in that the reaction of the first material with the second material is conducted in the presence of a metal salt, an ammonium salt or an acid.

24. The process according to claim 2, characterized in that the reaction of the first material with the second material is conducted in the presence of a metal salt, an ammonium salt or an acid.

25. The process according to claim 3, characterized in that the reaction of the first material with the second material is conducted in the presence of a metal salt, an ammonium salt or an acid.

26. The process according to claim 4, characterized in that the reaction of the first material with the second material is conducted in the presence of a metal salt, an ammonium salt or an acid.

27. The process according to claim 5, characterized in that the reaction of the first material with the second material is conducted in the presence of a metal salt, an ammonium salt or an acid.

28. The process according to claim 6, characterized in that the reaction of the first material with the second material is conducted in the presence of a metal salt, an ammonium salt or an acid.

29. The process according to claim 7, characterized in that the reaction of the first material with the second material is conducted in the presence of a metal salt, an ammonium salt or an acid.

30. The process according to claim 8, characterized in that the reaction of the first material with the second material is conducted in the presence of a metal salt, an ammonium salt or an acid.

* * * * *